United States Patent
Gear et al.

(10) Patent No.: US 12,419,917 B2
(45) Date of Patent: Sep. 23, 2025

(54) COMPOSITIONS AND METHODS FOR TREATMENT OF CONDITIONS USING FRACTIONATED HONEY

(71) Applicant: NDAL MFG INC, Monterey, CA (US)

(72) Inventors: Gavin Mark Gear, Monterey, CA (US); Roger Brett Edmonds, Auckland (NZ)

(73) Assignee: NDAL MFG INC, Monterey, CA (US)

( * ) Notice: Subject to any disclaimer, the term of this patent is extended or adjusted under 35 U.S.C. 154(b) by 228 days.

(21) Appl. No.: 17/725,377

(22) Filed: Apr. 20, 2022

(65) Prior Publication Data

US 2022/0339206 A1     Oct. 27, 2022

Related U.S. Application Data

(60) Provisional application No. 63/304,209, filed on Jan. 28, 2022, provisional application No. 63/178,973, filed on Apr. 23, 2021.

(51) Int. Cl.
| | |
|---|---|
| *A61K 35/644* | (2015.01) |
| *A61K 47/10* | (2017.01) |
| *A61K 47/12* | (2006.01) |
| *A61K 47/22* | (2006.01) |
| *A61P 31/00* | (2006.01) |

(52) U.S. Cl.
CPC ............ *A61K 35/644* (2013.01); *A61K 47/10* (2013.01); *A61K 47/12* (2013.01); *A61K 47/22* (2013.01); *A61P 31/00* (2018.01)

(58) Field of Classification Search
CPC ...... A61K 35/644; A61K 47/10; A61K 47/22; A61K 47/12; A61P 31/00
USPC ........................................................ 424/537
See application file for complete search history.

(56) References Cited

U.S. PATENT DOCUMENTS

| | | | |
|---|---|---|---|
| 4,875,620 A | 10/1989 | Lane, Sr. | |
| 5,356,650 A | 10/1994 | Kanayama | |
| 5,785,972 A | 7/1998 | Tyler | |
| 5,980,875 A | 11/1999 | Mousa | |
| 6,623,767 B1 | 9/2003 | Morice | |
| 8,568,790 B2 | 10/2013 | Moloney | |
| 8,609,159 B2 | 12/2013 | Sims et al. | |
| 8,632,810 B2 | 1/2014 | Moloney | |
| 8,663,717 B2 | 3/2014 | Adkins, Jr. et al. | |
| 8,815,298 B2 | 8/2014 | Moloney | |
| 9,044,489 B2 | 6/2015 | Moloney | |
| 9,469,675 B2 | 10/2016 | Bean et al. | |
| 9,580,464 B2 | 2/2017 | Johnson et al. | |
| 2003/0136274 A1 | 7/2003 | Caskey | |
| 2004/0121020 A1 | 6/2004 | Moloney | |
| 2006/0099166 A1 | 5/2006 | Vandeputte | |
| 2010/0233285 A1 | 9/2010 | Stuart et al. | |
| 2011/0159104 A1 | 6/2011 | Teslenko | |
| 2014/0127283 A1 | 5/2014 | Watson | |
| 2014/0199266 A1 | 7/2014 | Park et al. | |
| 2016/0220722 A1 | 8/2016 | Wardell et al. | |
| 2016/0331794 A1 | 11/2016 | Mercati et al. | |
| 2017/0087194 A1* | 3/2017 | Perlmutter | A61K 9/12 |

FOREIGN PATENT DOCUMENTS

| | | |
|---|---|---|
| AU | 2007100007 | 2/2007 |
| CN | 104522458 A | 4/2015 |
| CN | 109452601 A | 3/2019 |
| EP | 0355356 | 2/1990 |
| EP | 0460588 | 12/1991 |
| EP | 0489206 | 6/1992 |
| EP | 0909557 | 4/1999 |
| GB | 1378104 | 12/1974 |
| GB | 2382527 | 6/2003 |
| NZ | 502158 | 5/2002 |
| NZ | 337514 | 11/2002 |
| NZ | 505498 | 3/2003 |
| NZ | 546851 | 10/2007 |
| NZ | 545248 | 2/2008 |
| WO | WO9736501 | 10/1997 |
| WO | WO9955349 | 11/1999 |
| WO | WO0141776 | 6/2001 |
| WO | WO0167888 | 9/2001 |
| WO | WO0200269 | 1/2002 |
| WO | WO03047642 | 6/2003 |
| WO | 2005120250 | 12/2005 |
| WO | WO2007045931 | 4/2007 |

(Continued)

OTHER PUBLICATIONS

Department of Conservation, Te Papa Atawhai, Manuka/kahikātoa and kanuka, Apr. 18, 2008, Available online at: www.doc.govt.nz/nature/native-plants/manuka-kahikatoa-and-kanuka/.*

International Search Report and Written Opinion for International Application No. PCT/US2022/025827 mailed Jun. 14, 2022, 11 pages.

Johnston, Matthew, et al., "Antibacterial activity of Manuka honey and its components: An overview," AIMS Microbiology (2018), 4(4), 655-664.

Alvarez-Suarez, Jose M., et al., "The Composition and Biological Activity of Honey: A Focus on Manuka Honey," Foods (2014), 3, 420-432.

Bruce Boynton, "National Honey Board: Honey is Made from Nectar, Not Pollen", received from https://www.foodsafetynews.com/2012/04/national-honey-board-honey-is-made-from-nectar-not-pollen/, Apr. 23, 2012, 3 pages.

(Continued)

*Primary Examiner* — Jennifer M.H. Tichy
(74) *Attorney, Agent, or Firm* — Aikin & Gallant, LLP

(57) ABSTRACT

A method of treating a human suffering from an infection caused by a pathogen, the method comprising: administering to the human in need thereof a therapeutically effective amount of a composition comprising a fractionated honey, wherein the fractionated honey is produced from Leptospermum scoparium; wherein the fractionated honey does not undergo yeast fermentation normally associated with honey at moisture contents greater than 19% water by weight; and wherein the composition comprises between 19 weight % and 99 weight % water, and has a water activity of between 0.85 and 1.0, a pH between 3 and 4.5.

11 Claims, No Drawings

(56) References Cited

FOREIGN PATENT DOCUMENTS

| WO | 2008072988 | 6/2008 |
|---|---|---|
| WO | 2010044042 | 4/2010 |
| WO | 2013191565 | 12/2013 |
| WO | WO2015164981 | 11/2015 |

OTHER PUBLICATIONS

Emineke et al., "Diluted honey inhibits biofilm formation: potential application in urinary catheter management?", Received from https://jcp.bmj.com/content/70/2/140.long, Journal of Clinical Pathology. 2017, 14 pages.

Krushna et al., "Honey as a natural preservative of milk", received from https://nopr.niscpr.res.in/bitstream/123456789/5238/1/IJEB%2045%285%29%20459-464.pdf, received Aug. 31, 2005, Revised Oct. 27, 2006, 6 pages.

French et al., "The antibacterial activity of honey against coagulase-negative *Staphylococci*", received from https:// pubmed.ncbi.nlm.nih.gov/15941774/, Jun. 7, 2005., 8 pages.

Uskudar-Guclu et al., "Antibacterial, Antifungal and Antibiofilm Activity of Methylglyoxal: A Phytochemical from Manuka Honey" Mediterranean Journal of Infection, Microbes and Antimicrobials. Sep. 15, 2021, 7 pages.

Lee, Victoria S., et al., "Manuka honey versus saline sinus irrigation in the treatment of cystic fibrosis-associated chronic rhinosinusitis: A randomised pilot trial," Clinical Otolaryngology, Aug. 16, 2020, pp. 1-7.

Roberts, Aled E.L., et al., "Anti-pseudomonad Activity of Manuka Honey and Antibiotics in a Specialized ex vivo Model Simulating Cystic Fibrosis Lung Infection," Front Microbiol, 2019; 10: 869, Apr. 24, 2019, 16 pages.

Hammond, Eric N., et al., "Biofilm formation of *Clostridium difficile* and susceptibility to Manuka Honey," BMC Complementary & Alternative Medicine, 2014, 14:329, 6 pages.

Blackett, K.L., et al., "Oesophageal bacterial biofilm changes in gastro-oseophageal reflux disease, Barrett's and oesophageal carcinoma: association or causality?," Alimentary Pharmacology & Therapeutics, vol. 37, Issue 11, Apr. 22, 2013, 18 pages.

Bouzo, Daniel, et al., "Characterizing the Mechanism of Action of an Ancient Antimicrobial, Manuka Honey, against *Pseudomonas aeruginosa* Using Modern Transcriptomics," mSystems, May/Jun. 2020, vol. 5, Issue 3, Jun. 30, 2020, 16 pages.

Tiwari, Gaurav, et al., "Drug delivery systems: An updated review," International Journal of Pharmaceutical Investigation, Jan. 2012, vol. 2, Issue 1, 10 pages.

Thorarinsdottir, Hulda R., et al., "Biofilm formation on three different endotracheal tubes: a prospective clinical trial," Critical Care, (2020) 24:382, 12 pages.

Sakano, Takashi, et al., Above and beyond: biofilm and the ongoing search for strategies to reduce ventilator-associated pneumonia (VAP), Critical Care, (2020) 24:510, 3 pages.

Abedi F, Ghasemi S, Farkhondeh T, et al. Possible Potential Effects of Honey and Its Main Components Against Covid-19 Infection. Dose Response Int J. 2021;19(1): 1-13.

Adams CJ, Boult CH, Deadman BJ, et al. Isolation by HPLC and characterisation of the bioactive fraction of New Zealand manuka (*Leptospermum scoparium*) honey. Carbohydr Res. 2008;343(4):651-659.

Almasaudi SB, Abbas AT, Al-Hindi RR, et al. Manuka Honey Exerts Antioxidant and Anti-Inflammatory Activities That Promote Healing of Acetic Acid-Induced Gastric Ulcer in Rats. Evid Based Complement Alternat Med. 2017;2017:5413917.

Al-Hatamleh Mai, Hatmal MM, Sattar K, et al. Antiviral and Immunomodulatory Effects of Phytochemicals from Honey against COVID-19: Potential Mechanisms of Action and Future Directions. Molecules. 2020;25(21):0.

Al-Waili, N Al Ghamdi Al, Ansari MJ, et al. Differences in composition of honey samples and their impact on the antimicrobial activities against drug multi-resistant bacteria and pathogenic fungi. Arch Med Res. 2013;44(4):307-316.

Anon JB. Acute bacterial rhinosinusitis in pediatric medicine: current issues in diagnosis and management. Paediatr Drugs. 2003;5(Suppl 1):25-33 (Abstract).

Autoimmunity Research Foundation—Andre Levchenko, Biofilm Bacteria. Available at: https://mpkb.org/home/pathogenesis/microbiota/biofilm. Accessed Feb. 22, 2023. Last updated Sep. 14, 2020.

Blair SE, Cokcetin NN, Harry EJ, Carter DA. The unusual antibacterial activity of medical-grade Leptospermum honey: antibacterial spectrum, resistance and transcriptome analysis. Eur J Clin Microbiol Infect Dis. 2009;28(10):1199-1208.

Carter DA, Blair SE, Cokcetin NN, et al. Therapeutic Manuka honey: no longer so alternative. Frontiers in Microbiology. 2016;7:569.

Clardy J, Fischbach MA, Currie CR. The natural history of antibiotics. Curr Biol. 2009;19(11):R437-R441.

Cooper RA, Jenkins L, Henriques AF, et al. Absence of bacterial resistance to medical-grade manuka honey. Eur J Clin Microbiol Infect Dis. 2010;29(10):1237-1241.

Degen J, Vogel M, Richter D, et al. Metabolic transit of dietary methylglyoxal. J Agric Food Chem. 2013;61(43):10253-10260 (Abstract).

Foreman A, Boase S, Psaltis A, Wormald PJ. Role of Bacterial and Fungal Biofilms in Chronic Rhinosinusitis. Current Allergy Asthma Reports. 2012;12(2):127-135 (ABSTRACT).

Forrest RD. Early history of wound treatment. J R Soc Med. 1982;75(3):198.

Houssain KS, Hossain MG, Moni A, et al. Prospects of honey in fighting against COVID-19: pharmacological insights and therapeutic promises. Heliyon. 2020;6(12):e05798.

Huang WH, Hung PK. Methicillin-resistant *Staphylococcus aureus* infections in acute rhinosinusitis. Laryngoscope. 2006;116(2):288-291 (Abstract).

Kilty SJ, Al Mutari D, Duval M, et al. Manuka honey: Histological effect on respiratory mucosa. Am J Rhinol Allergy. 2010;24(3):247 (Abstract).

Kim S-Y and Kang S-S. Anti-biofilm activities of Manuka Honey against *Escherichia coli* O157:H7. Food Science Animal Resources. 2020;40(4):668-674.

Kwakman PH, te Velde AA, de Boer L, et al. How honey kills bacteria. Faseb J. 2010;24(7): 2576-2582 (Abstract).

Lee VS, Humphreys IM, Purcell PL, Davis GE. Manuka honey sinus irrigation for the treatment of chronic rhinosinusitis: a randomized controlled trial. Int Forum Allergy Rhinol. 2017;7(4):365-372.

Mavric E, Wittmann S, Barth G, Henle T Identification and quantification of methylglyoxal as the dominant antibacterial constituent of Manuka (*Leptospermum scoparium*) honeys from New Zealand. Mol Nutr Food Res. 2008;52(4):483-489.

Minden-Birkenmaier BA, Bowlin GL. Honey-based templates in wound healing and tissue engineering. Bioengineering (Basel). 2018;5(2):46.

Minden-Birkenmaier BA, Cherukuri K, Smith RA, et al. Manuka honey modules the inflammatory behavior of a dHL-60 neutrophil model under the cytotoxic limit. Int J Biomaterials. 2019a;6132581.

Minden-Birkenmaier BA, Meadows MB, Cherukuri K, et al. The Effect of Manuka Honey on dHL-60 Cytokine, Chemokine, and Matrix-Degrading Enzyme Release under Inflammatory Conditions. Med One. 2019b;4(2):e190005.

Molan P, Rhodes T. Honey: a biologic wound dressing. Wounds. 2015;27(6):141-151.

Ooi ML, Jothin A, Bennett C, et al. Manuka honey sinus irrigations in recalcitrant chronic rhinosinusitis: phase 1 randomized, single-blinded, placebo-controlled trial. Int Forum Allergy Rhinol. 2019;9(12):1470-1477 (Abstract).

Paramasivan S, Drilling AJ, Jardelesa C, et al. Methylglyoxal-augmented manuka honey as a topical anti-*Staphylococcus aureus* biofilm agent: safety and efficacy in an in vivo model. Int Forum Allergy Rhinol. 2014;4(3):187-195 (Abstract).

Ramadan Hassan H. Pediatric Sinusitis: Update. J Otolaryngol. 2005;34(Suppl1):S14-17 (Abstract).

(56) References Cited

OTHER PUBLICATIONS

Roberts AEL, Maddocks SE, Cooper RA. Manuka honey is bactericidal against Pesudomonas aeruginosa and results in differential expression of oprF and algD. Microbiol. 2012;158(Pt 12):3005-3013.

Roberts AEL, Brown HL, Jenkins RE. On the antibacterial effects of manuka honey: mechanistic insights. Research Reports Biol. 2015;6(2015):215-224.

Shahzad A, Cohrs RJ. In vitro antiviral activity of honey against varicella zoster virus (VZV): A translational medicine study for potential remedy for shingles. Transl Biomed. 2012;3(2):2.

Wallace A, Eady S, Miles M, et al. Demonstrating the safety of manuka honey UMF 20+ in a human clinical trial with healthy individuals. Br J Nutr. 2010;103(7):1023-1028.

Watanabe, Ken, et al., "Anti-influenza Viral Effects of Honey In Vitro: Potent High Activity of Manuka Honey," Archives of Medical Research 45 (2014) 359-365.

Enani, Sumia Mohammad, "Possible Prophylactic and Therapeutic Foods for Prevention and Management of COVID-19—An Updated Review," Current Research in Nutrition and Food Science 2020; 8(3). https://bit.ly/2IJMrVy.

Hou, Jiapeng, et al., "Bacterial Density and Biofilm Structure Determined by Optical Coherence Tomography," Scientific Reports (2019) 9:9794.

Kostakioti, Mara, et al., "Bacterial Biofilms: Development, Dispersal, and Therapeutic Strategies in the Dawn of the Postantibiotic Era," Cold Spring Harb Perspect Med. Apr. 2013; 3(4): a010306, 29 pages.

Levchenko, Andre, "Biofilm bacteria," The Marshall Protocol Knowledge Base Autoimmunity Research Foundation, <https://mpkb.org/home/pathogenesis/microbiota/biofilm>, 7 pages.

Bose, Sumit, et al., "Infectious Chronic Rhinosinusitis," J Allergy Clin Immunol Pract. Jul.-Aug. 2016; 4(4): 584-589.

Fastenberg, Judd H., "Biofilms in chronic rhinosinusitis: Pathophysiology and therapeutic strategies," World J Otorhinolaryngol Head Neck Surg. Dec. 2016; 2(4): 219-229.

Alandejani, T., et al., "Effectiveness of honey on Staphylococcus aureus and Pseudomonas aeruginosa biofilms, " Otolaryngol Head Neck Surg Jul. 2009; 141(1):114-8.

Lu, Jing, et al., "Manuka-type honeys can eradicate biofilms produced by Staphylococcus aureus strains with different biofilm-forming abilities, " PeerJ, Mar. 26, 2014, 25 pages.

U.S. Department of Health and Human Services Food and Drug Administration, "Antibacterial Therapies for Patients With an Unmet Medical Need for Treatment of Serious Bacterial Diseases, Guidance for Industry," Center for Drug Evaluation and Research (CDER), Aug. 2017, 19 pages.

U.S. Department of Health and Human Services Food and Drug Administration, "Limited Population Pathway for Antibacterial and Antifungal Drugs, Guidance for Industry," Center for Drug Evaluation and Research (CDER), Center for Biologics Evaluation and Research (CBER), Aug. 2020, 17 pages.

Examination Report No. 1 for Standard Patent Application, received for AU Application No. 2022261987, mailed on Aug. 19, 2024, 3 pages.

Goldman, Bruce, "Stanford Medicine scientists pinpoint COVD-19 virus's entry and exit ports inside our noses," Stanford Medicine News Center, <https://med.stanford.edu/news/all-news/2023/01/covid-virus-infection-nasal.html?utm_source=Stanford+ALL&utm_campaign=8b01a30253-int_COPY%E2%80%A6>, Jan. 5, 2023, 6 pages.

MPI 5 Attributes—Chemical and DNA Markers, retrieved online, https://www.analytica.co.nz/testing-services/honey/mpi-5-attributes-chemical-and-dna-markers/#:~:text=The%20MPI%20definition%20consists%20of,-floral%20M%C4%81nuka%2C%20for%20export, Analytica Laboratories, Ministry for Primary Industry, New Zealand Food Safety, Jul. 2018, 2 pages.

PCT/PCT/US2023/011560. "PCT Notification of Transmittal of the International Preliminary Report of Patentability and the Written Opinion of the International Searching Authority," mailed Jul. 30, 2024, 6 pages.

A. Cooper, et al.; "MP-13.18, Honey: A Potential Intravesical Therapeutic", Moderated Poster Session 13: Bladder Cancer 1, Urology. 2009, 74(4): SI08. DOI: 10.1016/j.urology.2009.07.1358.

H. Ranade, et al.; "Honey-based trap for Pseudomonas: a sustainable prototype for water disinfection", Archives of Microbiology. 2021, 203, 6061-6069. DOI: 10.1007/s00203-021-02568-0.

Examination Report No. 2 for Standard Patent Application, received for AU Application No. 2022261987, mailed on Oct. 29, 2024, 3 pages.

PCT International Preliminary Report of Patentability issued for PCT Patent Application No. PCT/US2023/011560, mailed on Aug. 8, 2024, 7 pages.

Extended European Search Report received for European Patent Application No. 22792529.4, mailed on Jan. 27, 2025, 10 pages.

Piotrowski et al. "Antimicrobial effects of Manuka honey on in vitro biofilm formation by Clostridium difficile," DOI 10.1007/s10096-017-2980-1, published online Apr. 18, 2017, Eur J Clin Microbiol Infect Dis (2017), 36: pp. 1661-1664.

Howse Steve, "Managing the Risk of Fermenting Honey;" Analytica Laboratories; United States Department of Agriculture. Revised Oct. 1980; Beekeeping in the United States; Agriculture Handbook No. 335; 2 pages.

Chirife et al.; "The Correlation Between Water Activity and % Moisture in Honey: Fundamental Aspects and Application to Argentine Honeys;" Journal of Food Engineering; vol. 72; Feb. 2006; pp. 287-292.

\* cited by examiner

COMPOSITIONS AND METHODS FOR TREATMENT OF CONDITIONS USING FRACTIONATED HONEY

BACKGROUND

Cross-Reference to Related Application

The application is a non-provisional application of U.S. Provisional Patent Application No. 63/304,209, filed Jan. 28, 2022, and U.S. Provisional Patent Application No. 63/178,973, filed Apr. 23, 2021, which are both incorporated herein by reference in their entirety.

Field

Compositions and methods for treating or preventing conditions caused by a pathogen including a bacterium, a virus or other causes using a fractionated honey.

Background

There are a number of respiratory infections humans suffer from on a regular basis. Such infections are commonly caused by pathogens including viruses and bacteria. For example, lung, nasal and/or sinus infections may be caused by one or more of rhinovirus, coronavirus, parainfluenza virus, respiratory syncytial virus, adenovirus, influenza viruses, enterovirus, metapneumovirus, coronavirus 229E, OC43, NL63 and HKU1, coronavirus COVID-19, MERS-CoV, SARS-CoV, influenza A & B viruses, parainfluenza type 1 & type 2, streptococcal, pneumococcal, staphylococcal, avian influenza H5, H7, H9 viruses, metapneumovirus, *Streptococci, pneumococci, Moraxella catarrhalis, staphylococci, Haemophilus influenzae, Moraxella catarrhalis, Staphylococci, Staphylococcus aureus, Klebsiella pneumoniae Pseudomonas aeruginosa, Proteus mirabilis, Enterobacter, Staphylococcus epidermidis, Propionibacterium acnes,* coagulase negative *Staphylococcus, Streptococcus pneumoniae,* Prevotella *Streptococcus, Veillonella,* gram negative bacilli and/or oropharyngeal anaerobic microorganisms. It is believed that many of the infections, and particularly chronic infections, caused by these viruses and/or bacteria or infectious, vasomotor, drug induced (eg, aspirin or nonsteroidal anti-inflammatory drug [NSAID]-induced) and atrophic rhinitis, are the result of biofilms forming on biotic surfaces, and specifically tissue surfaces within the respiratory tract. It is believed therefore that such infections and/or conditions may be alleviated by disrupting the cell structures and inhibiting the associated biofilms that form on the tissue surfaces. In addition, biofilms can form on non-living tissues or abiotic surfaces. For example, biofilms can form on metal or other non-living surfaces allowing pathogens to spread. For example, a biofilm may form on the surface of a medical implant or other foreign object introduced within the body and/or equipment used in a healthcare setting. Biofilms can therefore also be associated with infections within hospitalized patients and/or other patients in health care settings. A biofilm is essentially a cluster of bacteria held together by a mucus-like material that adheres the biofilm to the surface on which it forms. The production of biofilms is achieved through external signals followed by the activation of specific genes. In addition to respiratory infections, biofilms can be associated with infections in hospitalized patients, for example, they can form on artificial implants or other foreign objects introduced into the body causing severe infections.

SUMMARY

An aspect of the disclosure is directed to a method of treating a human suffering from an infection or disease caused by a pathogen, the method comprising: administering to the human in need thereof a therapeutically effective amount of a composition comprising a fractionated honey, wherein the fractionated honey is produced from Leptospermum scoparium; wherein the fractionated honey does not undergo yeast fermentation normally associated with honey at moisture contents greater than 19% water by weight; and wherein the composition comprises between 19 weight % and 99 weight % water, and has a water activity of between 0.85 and 1.0, a pH between 3 and 4.5. The infection may be a lung, a nasal or a sinus infection. The infection may be caused by a gram positive bacterium, a gram negative bacterium or a virus. The infection may be caused by a bacterium selected from the group consisting of *Staphylococcus aureus, Haemophilus influenza, Pseudomonas aeruginosa, Staphylococcus aureus, Staphylococcus epidermidis, Propionibacterium acnes,* coagulase negative *Staphylococcus, Streptococcus pneumoniae,* Prevotella *Streptococcus, Veillonella, Proteus mirabilis, Klebsiella pneumonia, Pneumocystis carinii,* cytomegalovirus, methicillin-resistant *Staphylococcus aureus* (MRSA), *Acinetobacter baumannii,* chlamydophila *pneumonia* or mycoplasma *pneumoniae.* The infection may be caused by a virus selected from the group consisting of severe acute respiratory syndrome coronavirus (SARS-CoV), sever acute respiratory syndrome coronavirus 2 (SARS-CoV-2), COVID-19, Middle East respiratory syndrome coronavirus (MERS-CoV), respiratory syncytial virus (RSV), Rhinoviruses, Parainfluenza viruses, Influenza viruses, and Adenoviruses. The fractionated honey may be produced by processing a Manuka honey to remove all DNA. The composition may include the fractionated honey in an amount of from 4 weight % to 80 weight % of the composition, and further comprises water, glycerin and an acid mixture. The acid mixture may include citric acid and ascorbic acid in amounts sufficient to prevent fermentation of the composition. The fractionated honey may be produced by processing a Manuka honey to remove all of a DNA marker from Manuka pollen. In some aspects, the fractionated honey may include methylglyoxal in an amount of at least 83 mg/kg.

In another aspect, a method of disrupting a biofilm caused by a pathogen to treat a human suffering from an infection or a disease is disclosed including administering to the human in need thereof a therapeutically effective amount of a composition comprising a fractionated honey produced from Leptospermum scoparium; and wherein the composition comprises a water activity of between 0.85 and 1.0, a pH between 3 and 4.5, and an acid mixture and or UV light to prevent fermentation. In some aspects, the infection may include a lung, a nasal or a sinus infection. The infection may be caused by a gram positive bacterium, a gram negative bacterium or a virus. In some aspects, the infection may be caused by a bacterium selected from the group consisting of *Staphylococcus aureus, Haemophilus influenza, Pseudomonas aeruginosa, Staphylococcus aureus, Staphylococcus epidermidis, Propionibacterium acnes,* coagulase negative *Staphylococcus, Streptococcus pneumoniae,* Prevotella *Streptococcus, Veillonella, Proteus mirabilis, Klebsiella pneumonia,* Pneumocystis carinii, cytomegalovirus, methicillin-resistant *Staphylococcus aureus* (MRSA), *Acinetobacter baumannii,* chlamydophila *pneumonia* or mycoplasma *pneumoniae.* In other aspects, the infection may be caused by a virus selected from the group consisting of severe acute respiratory syndrome coronavirus (SARS-CoV), sever acute respiratory syndrome coronavirus 2 (SARS-CoV-2), COVID-19, Middle East respiratory syndrome coronavirus (MERS-CoV), respiratory syncytial virus (RSV), Rhinoviruses, Parainfluenza viruses, Influenza viruses, and Adenoviruses. In some aspects, the composition may further include water, glycerin, citric acid and ascorbic acid. The fractionated honey may include a DNA marker level from Manuka pollen of zero. The fractionated honey may include methylglyoxal in an amount of at least 573 mg/kg.

In another aspect, a method of preventing an infection in a human caused by a pathogen, the method comprising: administering to the human in need thereof a therapeutically effective amount of a composition comprising a fractionated honey, wherein the fractionated honey is produced from Leptospermum scoparium; wherein the fractionated honey does not undergo yeast fermentation normally associated with honey at moisture contents greater than 19% water by weight; and wherein the composition comprises between 19 weight % and 99 weight % water, and has a water activity of between 0.85 and 1.0, a pH between 3 and 4.5. In some aspects, the infection may include nonallergic forms of perennial rhinitis including infectious, vasomotor, drug-induced and atrophic rhinitis. The infection may include rhinitis medicamentosa.

In another aspects, the invention is directed to a composition including an effective amount of a fractionated honey produced from Leptospermum scoparium in a dosage form sufficient to disrupt a biofilm caused by a bacteria or virus in order to treat a human suffering from an infection. In some aspects, the effective amount of the fractioned honey comprises a concentration of from 4 wt % to 80 wt % of the composition, and the composition further comprises: a water, a glycerin, a salt, and an acid mixture comprising citric acid and ascorbic acid; and wherein a water activity is between 0.85 and 1.0, a pH is between 3 and 4.5, and the citric acid and the ascorbic acid are present in the composition in amounts effective to prevent fermentation.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

DETAILED DESCRIPTION

In this section we shall explain several preferred embodiments of this invention. Whenever the compositions, formulations, methods and other aspects of the embodiments are not expressly defined, the scope of the invention is not limited only to the disclosed embodiments, rather may encompass what is well known in the art. Also, while numerous details are set forth, it is understood that some embodiments of the invention may be practiced without these details. In other instances, well-known chemicals, formulations, ingredients and techniques have not been described in detail so as not to obscure the understanding of this description.

In one aspect, the instant invention is directed to a composition and method of using fractionated honey to treat or prevent persons from suffering from a condition such as an infection associated with a biofilm by disrupting the bacterial cell culture and inhibiting the bacterial biofilm. The fractionated honey is considered "fractionated" in that it is formed by taking Manuka honey and removing the DNA marker (pollen) from the honey. Manuka honey typically includes a number of markers that must be present for it to be considered an authentic Manuka honey. Among these markers is the DNA level from Manuka pollen, which is typically less than Cq 36 for Manuka honey. In the proposed fractionated honey, this DNA marker is removed such that the DNA level from Manuka pollen is essentially zero. The resulting fractionated honey maintains all the health benefits of Manuka honey without some of the side effects that may be associated with pollen, for example, allergic reactions. In addition, in some instances where the honey may be irradiated to achieve sterility, the removal of the pollen may have other benefits. For example, when honey is irradiated the pollen or contaminate may explode and become particulate matter in the honey, or a contaminate with potential to cause inflammation. Thus, the removal of pollen reduces the potential for the pollen to cause potential contaminates that may lead to undesirable inflammation in instances where the honey is irradiated, and in turn reduce the overall effectiveness of the honey.

While all honey is believed to have health benefits, Manuka honey includes unique antibacterial ingredients not found in other honeys believed to make it have superior anti-bacterial, anti-inflammatory and/or anti-viral properties to other types of honey. In particular, Manuka honey is a plant specific honey made by bees who collect nectar from New Zealand's native Leptospermum scoparium plant. As a result, Manuka honey contains a unique anti-bacterial ingredient not found in other honeys that is believed to make it an effective antibiotic and wound healer. In particular, Manuka honey naturally contains methylglyoxal (MGO), which is a chemical known to have antibacterial properties. In particular, MGO is a highly reactive compound which can readily react with cellular molecules. The chemical reactions between MGO and cellular molecules in the bacteria, damages molecules needed for bacterial viability. MGO is also an indicator of other active antibacterial or antiviral fractions within the fractionated honey and the precise mode of action of certain active fractions remains unknown, we see only the result of those active fractions. The higher the MGO content, the higher the grade of the Manuka honey. The fractionated honey disclosed herein maintains the MGO content without any allergy inducing pollen, thus resulting in an effective antibacterial and anti-inflammatory without any of the undesirable side effects sometimes associated with honey.

It is proposed herein that the MGO present in the proposed fractionated honey helps to treat and/or prevent diseases and/or infections by disrupting the bacterial cell structure and/or attachment of biofilm and/or cellular death. The disease and/or infections that may cause a biofilm and are suitable for treatment using the fractionated honey may be caused by one or more of a bacteria (e.g., gram-positive or gram-negative) or a virus.

In still further aspects, the proposed fractionated honey composition may be used as a prophylactic or preventative measure to prevent the user from developing or contracting any of the conditions disclosed herein. For example, the fractionated honey composition may provide immune support when administered prior to an infection or condition by improving sinus health and protecting the sinuses against particulate matter, bacteria, viruses, bed mites, pet dander, dust, pollen and/or other allergens. Representatively, honey, and particularly Manuka honey, has been found to efficiently inhibit influenza virus replication, which is related to its virucidal effects. Watanabe K, et al., Anti-influenza Viral Effects of Honey In Vitro: Potent High Activity of Manuka Honey, Arch Med Res. 2014 Jul; 45(5):359-365.

Representative diseases, infections, viruses and/or bacteria that are suitable for treatment or prevention using the fractionated honey disclosed herein may include, but are not limited to, adenoviruses, avian influenza H5, H7, and H9 viruses, coronaviruses 229E, OC43, NL63, and HKU1, SARS-CoV-2, COVID-19, MERS-CoV, SARS-CoV, enteroviruses, influenza viruses, influenza A and B viruses, H3N2 (an influenza A virus), metapneumoviruses, parainfluenza virus, parainfluenza viruses for example paramyxoviruses classified as types 1, 2, 3, and 4, respiratory syncytial virus, rhinovirus, nonallergic (e.g., nonallergic forms of perennial rhinitis including infectious, vasomotor, drug-induced and atrophic rhinitis) or allergic rhinitis, acute rhinitis, streptococcal, pneumococcal, staphylococcal infections, chronic rhinitis, rhinoscleroma, rhinosporidiosis, atrophic rhinitis, vasomotor rhinitis, sinusitis, *Haemophilus influenza, influenza, Moraxella catarrhalis*, or *Staphylococci, parainfluenza, pneumococci*, rhinovirus, *Streptococci, enterobacter*, gram negative bacilli and/or oropharyngeal anaerobic microorganisms, *Klebsiella pneumoniae, Proteus mirabilis*, and *Propionibacterium acnes*, prevotella *Streptococcus, Pseudomonas aeruginosa, Staphylococcus aureus, Staphylococcus epidermidis*, coagulase negative *Staphylococcus, Streptococcus pneumonia* and/or *Veillonella*, Pneumocystis carinii, cytomegalovirus, methicillin-resistant *Staphylococcus aureus* (MRSA), *Acinetobacter baumannii*, chlamydophila *pneumonia* and/or mycoplasma *pneumoniae*.

For example, the diseases and/or infections may be caused by one or more bacterium and may include, but are not limited to, *Staphylococcus aureus, Haemophilus influenza, Pseudomonas aeruginosa, Staphylococcus epidermidis, Propionibacterium acnes*, coagulase negative *Staphylococcus, Streptococcus pneumoniae*, Prevotella *Streptococcus, Veillonella, Proteus mirabilis*, methicillin-resistant *Staphylococcus aureus* (MRSA) and/or *Klebsiella pneumonia*.

Diseases and/or infections that may cause a biofilm and are suitable for treatment using the fractionated honey disclosed herein may include, but are not limited to, those caused by viruses including, but not limited to, severe acute respiratory syndrome coronavirus (SARS-CoV), severe acute respiratory syndrome coronavirus 2 (SARS-CoV-2), Middle East respiratory syndrome coronavirus (MERS-CoV), respiratory syncytial virus (RSV), Rhinoviruses, Parainfluenza viruses, Influenza viruses, and/or Adenoviruses.

Representatively, it is proposed that the fractionated honey disclosed herein inhibits Staphylococcus aureus by interfering with the cell division process. Under optimal conditions, bacterial cells duplicate and segregate their chromosome, forming a proteinaceous ring (the septum) across the mid-cell, creating two still-joined daughter cells. The completion of cell division occurs when peptidoglycan (murein) hydrolases degrade the cell wall between the two daughter cells, allowing separation. Manuka honey has been shown to inhibit the activity (and not the expression) of murein hydrolase, causing a build-up of septated non-dividing cells.

In addition, it is proposed that where the infection is caused by *Pseudomonas aeruginosa*, the fractionated honey causes the *Pseudomonas aeruginosa* cells to lyse in its presence due to the reduction of a key structural protein. Representatively, in contrast to the mechanism observed in *Staphylococcus aureus*, studies have proposed an entirely different mechanism against *Pseudomonas aeruginosa*. *Pseudomonas aeruginosa* cells can tolerate higher concentrations of Manuka honey when compared to *Staphylococcus aureus*, with inhibitory concentrations causing the loss of cellular integrity, leading to extensive cell lysis and cell death. *Pseudomonas aeruginosa* modulates its structural integrity through the production of a key anchor protein: outer membrane protein F (OprF). This protein provides a vital link between the outer membrane and underlying peptidoglycan layer, ensuring cell envelope homeostasis and regular cell shape. Reduced OprF expression has been observed in populations treated with Manuka honey, and a concomitant increase in membrane blebbing and cell lysis has also been detected. The different mechanistic actions observed against Pseudomonas aeruginosa (compared to Staphylococcus aureus aureus) highlights the potential for multiple modes of action, and multiple inhibitory compounds in Manuka honey and, in turn, the fractionated honey disclosed herein.

Moreover, exposure to Manuka honey has been shown to have other effects against a range of organisms. Against *Pseudomonas aeruginosa*, manuka honey suppresses the class I master regulators (FleQ and FliA), inhibiting the regulatory cascade required for flagellum production and leading to a significant reduction in flagellated cells. This observation is of clinical significance as adhesion and cellular motility are required for invasive virulence. Invasive virulence is problematic, as it allows the dissemination of cells through the bloodstream (bacteremia) to internal organs, which can prove fatal; therefore, the potential to reduce this process is highly valuable. The ability of *Pseudomonas aeruginosa* to sequester iron from a host may also be prohibited through Manuka honey treatment, following the observation of reduced siderophore production in treated samples. Sub-inhibitory concentrations are shown to inhibit cellular binding with fibronectin through the loss of two streptococcal surface proteins, SoF and SfbI. In wound infections, high concentrations of fibronectin are observed; therefore the inability of *Streptococcus pyogenes* to bind to the host may impact on its pathogenicity.

In addition to the studies into *Staphylococcus aureus, Pseudomonas aeruginosa*, and *Streptococcus pyogenes*, a study into the global action of Manuka honey on *Escherichia coli* demonstrated that following exposure to Manuka honey, 2% of the genes were up-regulated, while 1% were down-regulated by twofold or more. Up-regulation appears to occur across genes involved in stress response; those genes down-regulated are thought to encode products involved in protein synthesis. Conversely, down-regulation (16-fold) of a universal stress protein A (UspA) in *Staphylococcus aureus* cells treated with honey was observed. Another study has shown large-scale down-regulation of critical virulence genes (enterotoxins, fibronectin-binding proteins, hemolysins, and lipases), with concomitant reductions in global regulators and quorum-sensing genes. These mechanistic effects, both lethal and non-lethal, are a testament to the inhibitory efficacy of Manuka honey (and the fractionated honey disclosed herein) and confirm its broad spectrum of effects. In addition to these inhibitory effects, the fractionated honey composition disclosed herein may reduce virulence, motility, and biofilm formation.

The fractionated honey composition disclosed herein may include additional improvements over typical honey formulations including an increased water activity level and/or decreased acidity, while still preventing the growth of harmful bacteria and preventing fermentation. By way of background, when the water content in honey is increased, honey is susceptible to fermentation, particularly at a water content of 19% and above. When water content and/or activity is lowered, the potential for fermentation is eliminated. In addition, increasing the acidity to pH levels of 4.6 or lower prevents the growth of harmful bacteria. For example, reducing the water activity of a food to below 0.85 (e.g., by adding a sugar or salt) and/or acidifying a food to a pH level of 4.6 or lower (e.g., by adding vinegar or lemon juice) will prevent harmful bacteria and help prevent fermentation. Alternatively, a chemical preservative can be added to protect the honey from fermenting.

In the proposed fractionated honey formulation, the water activity is maintained at a range greater than 0.85, for example, a range of from about 0.86 to about 1, for example, a range of from about 0.89 to about 0.9. In still further aspects the fractionated honey formulation may have a water content greater than 19% by weight. In addition, the pH range of the proposed fractionated honey formulation is maintained between about 3 to about 4, for example, a pH of about 3.2 to about 3.6, for example, a pH of around 3.4 to 3.5, or about 3.44. The reduced acidity and/or increased water activity of the proposed fractionated honey composition results in a composition which may be gentler and less irritating when applied to sensitive tissue linings (e.g., nasal passages).

The fermentation and/or bacterial growth is instead controlled by using a mixture of citric acid and ascorbic acid (e.g., vitamin C) which blocks access of the honey to the water. When the citric and ascorbic acid mixture is added to the water and absorbed into the water cells, the honey is blocked from accessing the water, thereby naturally preventing fermentation. The citric and ascorbic acid mixture therefore acts as a natural preservative for the formulation so that the fractionated honey formulation can maintain a low acidity and increased water activity, and without the need for sugars, salts or chemical preservatives.

In one aspect, the composition including the fractionated honey may include a synergistic combination of one or more of a water, fractionated medical grade Manuka honey, vegetable Glycerin, salt, and/or a mixture including citric acid and ascorbic acid (e.g., vitamin C), that when combined, have an effect greater than the sum of their separate effects at treating a human suffering from an infection (e.g., lung, nasal, sinus, etc), for example, an infection caused by one or more of *Staphylococcus aureus, Haemophilus influenza*, or *Pseudomonas aeruginosa, Staphylococcus epidermidis, Propionibacterium acnes*, coagulase negative *Staphylococcus, Streptococcus pneumoniae*, Prevotella *Streptococcus, Veillonella, Proteus mirabilis*, and/or *Klebsiella pneumonia*.

In one embodiment, the composition balances one or more of a water, fractionated medical grade Manuka honey, vegetable Glycerin, salt, and/or a mixture including citric acid and ascorbic acid (e.g., vitamin C) in amounts sufficient to effectively treat a human suffering from an infection (e.g., lung, nasal, sinus, etc), for example, an infection caused by one or more of *Staphylococcus aureus, Haemophilus influenza*, or *Pseudomonas aeruginosa, Staphylococcus epidermidis, Propionibacterium acnes*, coagulase negative *Staphylococcus, Streptococcus pneumoniae*, Prevotella *Streptococcus, Veillonella, Proteus mirabilis*, and/or *Klebsiella pneumonia*.

Representatively, in one aspect, the fractionated honey composition may be a composition including, among other ingredients, water. Water functions as a carrier or delivery mechanism of the honey. It is therefore desirable for the water content to be any amount that effectively delivers the honey to the desired tissue. For example, in the case where the formulation is delivered in the form of a nasal spray, the water may be in an amount that allows for a spray pump to deliver the formulation to the furthest sinus pockets. The water content should, however, remain low enough so as not to promote bacterial growth. The water may be a filtered water present in an amount of at least about 50 weight percent (wt %) of the composition or more, and in some cases 82 weight percent or less. In another aspect, the water may be considered present in a ratio of one.

In another aspect, the fractionated honey composition may be a composition including, among other ingredients, a fractionated honey. For example, the fractionated honey may be a Manuka honey that is processed to remove the DNA marker associated with Manuka pollen while still maintaining a desired concentration of the MGO antibacterial component found in the honey, as previously discussed. For example, the fractionated honey may include an MGO content of, for example, at least 83 mg/kg MGO, at least 115 mg/kg, at least 263 mg/kg, at least 400 mg/kg, at least 573 mg/kg, and more preferably at least 600 mg/kg or at least 700 mg/kg or more. The fractionated honey may be included in the composition in an amount found effective for treating infections. For example, the fractionated honey may be included in an amount of at least 20 wt % of the composition. In another aspect, the fractionated honey may be considered present in a ratio of 1.41.

It should be understood that there is a direct relationship between the MGO content and the antibacterial and antiviral effect of honey. As previously discussed, typically a bacterial biofilm forms on a viral infection. The virus kills tissue, creating a breeding ground for the bacteria. An MGO 600 content is believed to kill the virus and the biofilm. One representative study in which the fractionated honey composition disclosed herein was found to exhibit virucidal activity when tested against SARS-CoV-2 will be disclosed in more detail in reference to Example 2.

In one aspect, the fractionated honey composition may be a composition including, among other ingredients, a glycerin. For example, the glycerin may be a vegetable glycerin. Glycerin is a tissue moisturizer and may be included in the composition to promote water absorption into tissues and for a soothing effect on the tissue. The glycerin may be included in the composition in an amount suitable for having a moisturizing and/or soothing effect on the tissue and/or found effective for treating infections. For example, the glycerin may be included in the composition in an amount of about 10% or less of the composition. In another aspect, the glycerin may be considered present in a ratio of 1.26.

In another aspect, the fractionated honey composition may be a composition including, among other ingredients, a salt. For example, the salt may be a pharmaceutical grade salt. The salt may be included in the composition in an amount found effective for treating infections. Salt may be included in the formulation to inhibit planktonic bacteria, open cells and/or to serve as a flushing agent when in solution with water. For example, the salt may be included in the composition in an amount of about 5% or less of the composition. In another aspect, the salt may be considered present in a ratio of 1. In another aspect, the fractionated honey composition may be a composition including, among other ingredients, a mixture of citric acid and ascorbic acid. For example, the ascorbic acid may be vitamin C. The mixture may further include an amount of water, for example, from 40 wt % to 50 wt % water. The mixture of citric acid, ascorbic acid and water may be referred to herein as the "acid mixture". The acid mixture may be included in an amount and/or ratio found effective for blocking the access of the fractionated honey to water molecules and therefore prevent fermentation and/or bacterial growth. For example, the acid mixture may be included in the composition in an amount of about 1 wt % of the composition or less. In another aspect, the acid mixture may be considered present in a ratio of 1. Other ingredients or agents included in the composition that may not be specifically discussed above are included and described in reference to the exemplary formulations set forth below. In addition, it should further be understood that although the ingredients and/or agents described herein are categorized according to a single function, many have multiple functions and therefore may be understood to be included under other functional categories than those listed herein.

The following specific example sets forth an exemplary composition that may be administered to a subject and/or otherwise used to disrupt a biofilm formed on a tissue or abiotic surface. The ingredient amounts disclosed in the following example are in effective amounts suitable for disruption of a biofilm formed on a tissue or abiotic surface, and/or prevention or treatment of a human suffering from an infection (e.g., lung, nasal, sinus, etc) caused by one or more of the previously discussed viruses, bacteria, or other conditions, including, but not limited to, *Staphylococcus aureus, Haemophilus influenza,* or *Pseudomonas aeruginosa, Staphylococcus epidermidis, Propionibacterium acnes,* coagulase negative *Staphylococcus, Streptococcus pneumoniae,* Prevotella *Streptococcus, Veillonella, Proteus mirabilis, Klebsiella pneumoniae,* Pneumocystis carinii, cytomegalovirus, methicillin-resistant *Staphylococcus aureus* (MRSA), *Acinetobacter baumannii,* chlamydophila *pneumonia* and/or mycoplasma *pneumoniae* and/or otherwise improving the condition of the area to which the composition is applied. In one embodiment, the composition may have the following exemplary formulations:

EXAMPLE 1

| INGREDIENT | EFFECTIVE AMOUNT (weight % of the composition) |
|---|---|
| Filtered Water | 50 wt % or more |
| Fractionated Manuka Honey | 20 wt % or more |
| Vegetable Glycerin | 5 wt % or less |
| Pharmaceutical Grade Salt | 1 wt % or less |
| Acid Mixture | 1 wt % or less |

EXAMPLE 2

| INGREDIENT | EFFECTIVE AMOUNT (weight % of the composition) |
|---|---|
| Filtered Water | 50 wt % or more |
| Fractionated Manuka Honey | 25 wt % or less |
| Vegetable Glycerin | 5 wt % or less |
| Pharmaceutical Grade Salt | 1 wt % or less |
| Acid Mixture | 1 wt % or less |

EXAMPLE 3

| INGREDIENT | EFFECTIVE AMOUNT (weight % of the composition) |
|---|---|
| Filtered Water | 50 wt % or more |
| Fractionated Manuka Honey | 50 wt % or less |
| Vegetable Glycerin | 5 wt % or less |
| Pharmaceutical Grade Salt | 1 wt % or less |
| Acid Mixture | 1 wt % or less |

EXAMPLE 4

| INGREDIENT | EFFECTIVE AMOUNT (weight % of the composition) |
|---|---|
| Filtered Water | 20 wt % or more |
| Fractionated Manuka Honey | 75 wt % or less |
| Vegetable Glycerin | 5 wt % or less |
| Pharmaceutical Grade Salt | 1 wt % or less |
| Acid Mixture | 1 wt % or less |

EXAMPLE 5

| INGREDIENT | EFFECTIVE AMOUNT (weight % of the composition) |
|---|---|
| Filtered Water | 10 wt % or more |
| Fractionated Manuka Honey | 80 wt % or less |
| Vegetable Glycerin | 5 wt % or less |
| Pharmaceutical Grade Salt | 1 wt % or less |
| Acid Mixture | 2 wt % or less |

EXAMPLE 6

| INGREDIENT | EFFECTIVE AMOUNT (weight % of the composition) |
|---|---|
| Filtered Water | 20 wt % or less |
| Fractionated Manuka Honey | 20 wt % to 80 wt % |
| Vegetable Glycerin | 5 wt % or less |
| Pharmaceutical Grade Salt | 1 wt % or less |
| Acid Mixture | 3 wt % or less |

EXAMPLE 7

| INGREDIENT | EFFECTIVE AMOUNT (weight % of the composition) |
|---|---|
| Filtered Water | 50 wt % or more |
| Fractionated Manuka Honey | 4 wt % or more |
| Vegetable Glycerin | 5 wt % or less |
| Pharmaceutical Grade Salt | 1 wt % or less |
| Acid Mixture | 2 wt % or less |

In one representative study, it was found that the fractionated honey composition disclosed herein exhibited virucidal activity when tested against SARS-CoV-2 and/or effectively disrupted a biofilm. One representative study will now be described by way of the following non-limiting example.

EXAMPLE 8

Procedure
Virus, Media, and Cells

SARS-CoV-2 virus stocks were prepared by growing virus in Vero 76 cells. Test media used was MEM supplemented with 2% FBS and 50 µg/mL gentamicin.

Virucidal Assay

The fractionated honey composition was tested at full strength. SARS-CoV-2 virus stock was added to triplicate tubes of the sample so that there was 90% virus solution by volume and 10% prepared sample. Media only was added to one tube of each prepared concentration to serve as toxicity controls. Ethanol was tested in parallel as a positive control and water only to serve as the virus control. The compound and virus were incubated at room temperature for 1 hour. Following the contact period, the solutions were neutralized by a 1/10 dilution in test media.

Virus Quantification

Surviving virus was quantified by standard end-point dilution assay. Neutralized samples were combined for quantification for the average of triplicate tests. Samples were serially diluted using eight 10-fold dilutions in test medium. Each dilution was added to 4 wells of a 96-well plate with 80-100% confluent Vero 76 cells. The toxicity controls were added to an additional 4 wells and 2 of these wells were infected with virus to serve as neutralization controls, ensuring that residual sample in the titer assay plated did not inhibit growth and detection of surviving virus.

Plates were incubated at 37 ±2 degrees C. with 5% CO2. On day 6 after infection plates were scored for presence or absence of viral cytopathic effect (CPE). The Reed-Muench method was used to determine end-point titers (50% cell culture infectious dose, CCID50) of the samples, and the log reduction value (LRV) of the compound compared to the negative (water) control was calculated.

Controls

Virus controls were tested in water and the reduction of virus in test wells compared to virus controls was calculated as the log reduction value (LRV). Toxicity controls were tested with media not containing virus to see if the samples were toxic to cells. Neutralization controls were tested to ensure that virus inactivation did not continue after the specified contact time, and that residual sample in the titer assay plates did not inhibit growth and detection of surviving virus. This was done by adding toxicity samples to titer test plates then spiking each well with a low amount of virus that would produce an observable amount of CPE during the incubation period.

Results

Virus titer and log reduction value (LRV) for samples tested against SARS-CoV-2 are shown in Table 1. The average virus control titer was 5.0 log CCID50 per 0.1 mL and this was used for comparison of all test sample titers to determine LRV. Samples with <1 log reduction are not considered active for virucidal activity.

The limit of detection of virus was 0.7 log CC ID50 per 0.1 m L. The fractionated honey composition exhibited virucidal activity when tested against SARS-CoV-2, reducing virus titer by 1.0 logs (90%), though not below the limit of detection of the assay.

Neutralization controls demonstrated that residual sample did not inhibit virus growth and detection in the endpoint titer assays in wells that did not have cytotoxicity. Positive controls performed as expected.

TABLE 1

Virucidal efficacy of Manuka honey sinus cleanser against SARS-CoV-2 after incubation with virus at 22 ± 2° C.

| Compound | Concentration | Contact Time | Toxicity[a] | Neut. Control[b] | Virus Titer[c] | VC Titer[c] | LRV[d] |
|---|---|---|---|---|---|---|---|
| Manuka honey sinus cleanser | 100% | 1-hour | None | None | 4.0 | 5.0 | 1.0 |
| Ethanol | 70% | 1-hour | None | None | <0.7 | 5.0 | >4.3 |

[a]Cytotoxocity indicates the highest dilution of the endpoint titer where full (80-100%) cytotoxicity was observed
[b]Neutralization control indicates the highest dilution of the endpoint titer where compound inhibited virus CPE in wells after neutralization (ignored for calculation of virus titer and LRV)
[c]Virus titer of test sample or virus control (VC) in $\log_{10}$ $CCID_{50}$ of virus per 0.1 mL
[d]LRV (log reduction value) is the reduction of virus in test sample compared to the virus control

EXAMPLE 9

In another representative study, the fractionated honey composition disclosed herein may be tested for antibacterial activity against pathogens that cause rhinosinusitis and, therefore, may improve rhinitis symptoms in patients having the disease. One representative study will now be described by way of the following non-limiting example.

By way of background, rhinosinusitis is an umbrella term defining a group of upper airway diseases characterized by two or more sinonasal symptoms that are usually caused by mucosal inflammation and are characterized as resulting in nasal congestion, nasal obstruction, rhinorrhea, nasal pruritus, sneezing, and loss of sense of smell. The symptoms occur for two or more consecutive days and for more than one hour on most days, resolving in 12 days or less. Acute rhinosinusitis is present for 4 weeks or less, and subacute rhinosinusitis is defined as the above symptoms for four to 12 weeks. Chronic rhinosinusitis (CRS) is defined as inflammation of the nose and paranasal sinuses and is characterized by two or more of the above symptoms for 12 or more consecutive weeks.

Rhinosinusitis phenotypes result from a variety of etiologies including infections (viral/bacterial/fungal), allergic reactions, medications, hormone imbalance, and neural inflammatory dysfunction. It can be classified into three major phenotypes: infectious rhinosinusitis, allergic rhinosinusitis (ARS), and non-allergic rhinosinusitis (NARS). Rhinosinusitis significantly impacts quality of life, including sleep, work productivity, and school performance with significant psychological impairment.

It is believed based on evidence from the literature and anecdotal clinical trial data that the fractionated honey composition disclosed herein has antibacterial activity against pathogens that cause rhinosinusitis and, therefore, may improve rhinitis symptoms in patients having the disease. Some of this preliminary data may indicate that the fractionated honey composition disclosed herein interferes with bacterial biofilm formation and/or durability of the biofilm. This could help as a biomarker of bioactivity to use in a clinical development program as an outcome.

One representative study proposal may include the intended population of rhinosinusitis patients, 18 years of age and older, with mild, uncomplicated disease. The fractionated honey composition disclosed herein may be used as either an add-on to Standard of Care (SoC) therapy or as monotherapy (i.e., as the sole treatment for the disease). It is believed that successful treatment with the fractionated honey composition disclosed herein will include reduction of symptoms and corticosteroid use and avoidance of surgery, as well as improved quality of life. Potential study designs and patient-reported outcomes, and patient numbers may include the following non-limiting examples.

Trial design: Blinding of the treatment and control groups so there is no bias in identifying one group from another; for example, a randomized, double-blind, placebo-controlled trial with parallel groups.

Treatment duration: The study may be performed for at least 2 to 4 weeks in mild cases and up to 24 weeks or longer for patients with nasal polyps.

Dosing regimen: The dosing regimen may include a starting dose and dosages according to any of the fractionated honey formulations disclosed herein.

Primary outcome(s): In mild subjects would recommend Total Symptom Score (TSS) based on changes in 3 to 4 sinonasal symptoms over the treatment period. In subjects with polyps, the co-primary endpoints of a PRO of nasal congestion and a Nasal Polyp Score based on an endoscopic nasal polyp rating system that has been used in clinical trials may be used.

Secondary outcomes: Measurements of individual symptoms such as nasal blockage, smell, nasal discharge, facial pain or pressure, and rescue medication requirements may be used during the study. Change in imaging CT scans showing improvement in mucosal thickening, bone changes, air/fluid levels, and 3D volumetric CT score may also be included as an outcome. Patient-reported outcomes and health-related quality of life (HR-QOL) may also be provided.

Patient numbers: The estimated patient numbers may be based on the established dosing regimen along with an estimated value of the treatment effect seen in a biomarker assay either in in vitro studies or in animal models.

Based on the results of the initial study, further studies may be conducted to narrow the dose choices, based on the efficacy and safety data of the fractionated honey composition used in the initial study. The further study designs may be a double-blind, randomized, placebo-controlled trial with parallel groups. The efficacy and safety endpoints from the earlier study may be selected. Two replicated studies that have statistically significant efficacy and safety values of the primary endpoint(s), and subjects have tolerated the treatment with is efficacious effects so far, may also be conducted. These two trials may have the same trial designs, approximately the same number and type of patients for each treatment arm, similar treatment duration, one or more doses in common to compare, and the same efficacy and safety endpoints. The patient populations may be as diverse as possible.

In another representative study, it was found that the fractionated honey composition disclosed herein effectively disrupted biofilms in an abiotic system and it is therefore believed similar results could be achieved in biotic systems. One representative study evidencing the effectiveness of the composition in disrupting biofilms in abiotic systems, the results of which are believed to be applicable to biotic systems, will now be described by way of the following non-limiting example.

EXAMPLE 10

Procedure

The fractionated honey com positions or formulations described in the examples disclosed herein, and specifically compositions including the Fractionated honey concentrations of 50 wt % and 75 wt % were tested to determine the efficacy of the formulations against a mature Pseudomonas aeruginosa biofilm. The biofilm was grown on borosilicate glass coupons in a CDC biofilm reactor according to ASTM Method E3161-18. After 48 hours of growth, the efficacy of the composition against a mature biofilm was determined according to ASTM Method E2871-19. These methods are common and described in the "EPA Methods and Guidance for Testing the Efficacy of Antimicrobials against Biofilm Bacteria on Hard, Non-Porous Surfaces", which can be found at https://www.epa.gov/pesticides/methods-and-guidance-testing-efficacy-antimicrobials-against-biofilm-bacteria-hard-non. The testing included two contact times of 60 and 90 minutes. Products were neutralized using DE neutralizing broth. The same diluent used to treat the product may also be used for the control coupons. Treatments were performed at room temperature with no mixing. The results were reported as the biofilm log density for each coupon and the calculated mean log reduction in viable cells for product.

Discussion of Results

During the study, 60 and 90 minute control coupons were colonized with a log 8.7 and log 8.61 CFU/cm2 biofilm, which is the expected level of colonization with this biofilm growth method. A maximum log reduction of 0.85 for a treatment using the compositions including the Fractionated honey concentrations of 50 wt % at the 90 minute exposure time was found. A 0.85 log reduction means that 85.9% of the cells were killed, 14.1% remained viable. Micrographs from the experiment indicated that much of the dead biofilm cells remained on the surface after treatment with the agents tested. For imaging, the biofilms on all coupons were stained with a Live:Dead stain. This stain uses two fluorescent dyes which ostensibly differentiate between living and dead bacterial cells. Dead cells are intended to stain red while living cells are intended to stain green. The micrographs showed mainly green cells in the control coupons and mainly red-stained cells in the treated micrographs, suggesting many of the treated cells were not living.

It is further believed that a fractionated honey concentration of 25 wt % may be even more effective at disrupting biofilms. In addition, it is believed that a reduction in viable biofilm will result from each concentration of the formulation contact time combination. It is therefore believed that compositions and/or formulations including fractionated honey concentrations of 25 wt % to 75 wt %, for example, 25 wt %, 50 wt % and/or 75 wt %, as disclosed herein, can be used to successfully disrupt and/or otherwise disrupt biofilms on abiotic or biotic surfaces.

In one embodiment, the composition is administered to a human by any technique suitable for introducing the composition to the human in a form suitable for treatment of the desired infection. Representatively, the composition may be administered via an intranasal, oral, or dermal administration route. For example, in some aspects, the composition may be administered to the nasal and sinus passages using a nasal spray pump with the capacity to spray the total formulation in various strengths or percentages of honey, into the furthest sinus pockets. Representatively, the formulation or com position may be administered using multiple dosing methods, for example, several (e.g., two) back to back pumps per nostril, repeating back to back pumps hourly, repeating several times a day (e.g., three times a day), and/or repeating times a day for several days (e.g., three times a day for three days). In other aspects, the formulation may be administered to a wound, inside or on the body, using, for example, a medical device implant and/or a non-aerosol spray can, where the pressure is provided via an air bag within the can while keeping the composition isolated. In still further aspects, the composition may be delivered to the eye using a squeeze bottle for ophthalmological ingredients or an eye dropper and bottle for ophthalmological ingredients. In still further aspects, the composition may be administered to the lungs by way of a nebulizer or ventilator. In other aspects, the composition may be administered to the throat as an oral spray by mouth, for example, to the back of the throat. Alternatively, the composition may be administered into a body cavity by way of, for example, a catheter or other insertable medical device using a non-aerosol can. The composition can be made stronger in application via any of the above methods. It should further be understood that the administration routes and/or mechanisms described herein are intended as examples and should not be understood as the only suitable administration routes and/or mechanisms. Rather any administration route and/or mechanism suitable for use with the composition to treat a desired condition is contemplated.

The composition may be formed by mixing the fractionated honey composition with a vehicle until a concentration of the fractionated honey effective for treating the infection is achieved. Representatively, the composition may be mixed with a vehicle such that it includes at least 4 wt %, at least 20 wt %, at least 25 wt %, at least 50 wt %, at least 75 wt % or 80 wt % or less of fractionated honey.

The composition may be administered by any of the above routes pursuant to a regimen for administering the fractionated honey in an amount suitable for treating infection. Representatively, the composition may be administered to the human periodically. In some embodiments the composition is administered to the human once a day. In other embodiments, the composition is administered to the human once a day or more. For example, the composition may be administered multiple times a day until the infection is reduced. It is contemplated that the frequency and duration of administration of the composition may vary depending upon the amount of treatment agent in the composition, the desired effects, the health of the user's immune system and the particular viral or bacterial type of infection desired to be treated, prevented or otherwise affected.

In some embodiments, the composition is in the form of a pill, a capsule, a tablet, or a lozenge. The composition may further be administered in the form of a powder. In other embodiments, the composition is administered in the form of an aqueous solution. In some embodiments, the treatment agent in the form of a powder or aqueous solution may be incorporated into a candy bar, food bar, or power bar along with substances typically used in those items, such as grains, fruits, flavorings, nuts, binders, etc. In still further embodiments, the composition is administered in the form of an implant implanted within the mammal which releases a desired amount of the treatment agent over time or a dressing or patch. It is contemplated that the form of the composition may vary depending upon the desired administration route. Representatively, where the composition is to be injected into the tissue of the mammal, the composition may be in the form of an aqueous solution.

It should be appreciated that reference throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention.

In the foregoing specification, the invention has been described with reference to specific embodiments thereof. It will, however, be evident that various modifications and changes can be made thereto without departing from the broader spirit and scope of the invention as set forth in the appended claims. The specification and drawing are, accordingly, to be regarded in an illustrative rather than a restrictive sense.

The invention claimed is:

1. A method of treating a human suffering from an infection or disease caused by a pathogen, the method comprising:
   administering to the human in need thereof a therapeutically effective amount of a composition comprising a fractionated honey,
   wherein the fractionated honey is *Leptospermum scoparium* honey and is free of all DNA markers for *Leptospermum scoparium* pollen;
   wherein the fractionated honey does not undergo yeast fermentation associated with honey at moisture contents greater than 19% water by weight; and
   wherein the composition comprises between 19 weight % and 99 weight % water, and has a water activity of between 0.85 and 1.0, and a pH between 3 and 4.5.

2. The method of claim 1 wherein the infection comprises a lung, a nasal or a sinus infection, and the composition is administered in the form of a spray via an intranasal or an oral route.

3. The method of claim 1 wherein the infection is caused by a gram positive bacterium, a gram negative bacterium or a virus.

4. The method of claim 1 wherein the infection is caused by a bacterium selected from the group consisting of *Staphylococcus aureus, Haemophilus influenza, Pseudomonas aeruginosa, Staphylococcus epidermidis, Propionibacterium acnes*, coagulase negative *Staphylococcus, Streptococcus pneumoniae, Prevotella Streptococcus, Veillonella, Proteus mirabilis, Klebsiella pneumonia, Pneumocystis carinii*, cytomegalovirus, methicillin-resistant *Staphylococcus aureus* (MRSA), *Acinetobacter baumannii, chlamydophila* pneumonia or *Mycoplasma pneumoniae*.

5. The method of claim 1 wherein the infection is caused by a virus selected from the group consisting of severe acute respiratory syndrome coronavirus (SARS-COV), sever acute respiratory syndrome coronavirus 2 (SARS-COV-2), COVID-19, Middle East respiratory syndrome coronavirus (MERS-COV), respiratory syncytial virus (RSV), Rhinoviruses, Parainfluenza viruses, Influenza viruses, and Adenoviruses.

6. The method of claim 1 wherein the composition comprises the fractionated honey in an amount of from 4 weight % to 80 weight % of the composition, and further comprises water in an amount of 50 weight % to 82 weight %, glycerin in an amount of 5 weight % to 10 weight %, and an acid mixture in an amount of 1 weight % to 3 weight %.

7. The method of claim 6 wherein the acid mixture comprises citric acid and ascorbic acid in amounts sufficient to prevent fermentation of the composition.

8. The method of claim 1 wherein the composition is free of a chemical preservative.

9. The method of claim 1 wherein the fractionated honey comprises methylglyoxal in an amount of at least 83 mg/kg.

10. The method of claim 1 wherein the fractionated honey comprises methylglyoxal in an amount of at least 573 mg/kg.

11. A method of preventing an infection in a human caused by a pathogen, the method comprising:
- administering to the human in need thereof a therapeutically effective amount of a composition comprising a fractionated honey,
- wherein the fractionated honey is *Leptospermum scoparium* honey and is free of all DNA markers for *Leptospermum scoparium* pollen;
- wherein the fractionated honey does not undergo yeast fermentation associated with honey at moisture contents greater than 19% water by weight;
- wherein the composition comprises between 19 weight % and 99 weight % water, and has a water activity of between 0.85 and 1.0, a pH between 3 and 4.5; and
- wherein the infection comprises nonallergic forms of perennial rhinitis including infectious, vasomotor, drug-induced or atrophic rhinitis, or the infection comprises rhinitis medicamentosa.

\* \* \* \* \*